United States Patent [19]

Sarges

[11] Patent Number: 4,474,967

[45] Date of Patent: Oct. 2, 1984

[54] 8-DEUTERO AND 8-TRITIO-SUBSTITUTED DERIVATIVES OF D-4S-6-FLUORO-SPIRO[CHROMAN-4,4'-IMIDAZOLIDINE]-2',5'-DIONE

[75] Inventor: Reinhard Sarges, Mystic, Conn.

[73] Assignee: Pfizer Inc., New York, N.Y.

[21] Appl. No.: 488,947

[22] Filed: Apr. 27, 1983

[51] Int. Cl.$^3$ ........................................ C07D 491/107
[52] U.S. Cl. ................................. 548/309; 424/273 R
[58] Field of Search ..................... 548/309; 424/273 R

[56] References Cited

U.S. PATENT DOCUMENTS

| | | | |
|---|---|---|---|
| 3,821,383 | 6/1974 | Sestanj et al. | 424/258 |
| 4,117,230 | 9/1978 | Sarges | 548/309 |
| 4,130,714 | 12/1978 | Sarges | 548/309 |

FOREIGN PATENT DOCUMENTS 2080304  2/1982  United Kingdom .

Primary Examiner—Henry R. Jiles
Assistant Examiner—J. G. Mullins
Attorney, Agent, or Firm—Charles J. Knuth; Peter C. Richardson

[57] ABSTRACT

The 8-deutero, and 8-tritio-substituted derivatives of D-4S-6-fluoro-spiro-[chroman-4,4'-imidazolidine]-2',5'-dione (sorbinil) have been prepared. These compounds all have the 4S-configuration and are of value in the field of medicinal chemistry as aldose reductase inhibitors for the control of chronic diabetic complications. The labeled 8-deutero and 8-tritio derivatives are useful in metabolism pharmacokinetic studies and in binding studies with the drug in animals and man. The 8-halo derivatives are useful as intermediates for the labeled forms of the drug, in addition to being potent aldose reductase inhibitors per se. Methods for the preparation of these compounds are provided in some detail.

3 Claims, No Drawings

8-DEUTERO AND 8-TRITIO-SUBSTITUTED DERIVATIVES OF D-4S-6-FLUORO-SPIRO[CHROMAN-4,4'-IMIDAZOLIDINE]-2',5'-DIONE

BACKGROUND OF THE INVENTION

This invention relates to new and useful optically-active hydantoin derivatives in the field of medicinal chemistry. More particularly, it is concerned with certain novel 8-substituted derivatives of D-6-fluoro-spiro-[chroman-4,4'-imidazolidine]-2',5'-dione, which are of especial value in view of their therapeutic and physical-chemical properties.

In the past, various attempts have been made by numerous investigators in the field of organic medicinal chemistry to obtain new and better oral antidiabetic agents. For the most part, these efforts have involved the synthesis and testing of various heretofore new and unavailable organic compounds, particularly in the area of the sulfonylureas, in an endeavor to determine their ability to lower blood sugar (i.e., glucose) levels to a substantially high degree when given by the oral route of administration. However, in the search for newer and still more effective antidiabetic agents, little is known about the effect of other organic compounds in preventing or arresting certain chronic complications of diabetes, such as diabetic cataracts, neuropathy and retinopathy, etc. Nevertheless, K. Sestanj et al. in U.S. Pat. No. 3,821,383 do disclose that certain aldose reductase inhibitors like 1,3-dioxo-1H-benz[d,e]-isoquinoline-2(3)-acetic acid and some closely-related derivatives thereof are useful for these purposes even though these particular compounds are not known to be hypoglycemic. These particular aldose reductase inhibitors function by inhibiting the activity of the enzyme aldose reductase, which is primarily responsible for regulating the reduction of aldoses (like glucose and galactose) to the corresponding polyols (such as sorbitol and galactitol) in the human body. In this way, unwanted accumulations of galactitol in the lens of galactosemic subjects and of sorbitol in the lens, peripheral nervous cord and kidney of various diabetic subjects are prevented or reduced. As a result, these compounds are of value as aldose reductase inhibitors for controlling certain chronic diabetic complications, including those of an ocular nature, since it is already known in the art that the presence of polyols in the lens of the eye leads to cataract formation together with a concomitant loss of lens clarity.

More recently, there is disclosed by R. Sarges in U.S. Pat. Nos. 4,117,230 and 4,130,714 a series of spiro-hydantoin compounds which are useful as aldose reductase inhibitors for controlling certain chronic diabetic complications. The key compound disclosed in U.S. Pat. No. 4,117,230 is dl-6-fluoro-[chroman-4,4'-imidazolidine]-2',5'-dione, while the key compound disclosed in U.S. Pat. No. 4,130,714 is the corresponding dextrorotatory isomer. The latter compound, viz., d-6-fluoro-[chroman-4,4'-imidazolidine]-2',5'-dione or sorbinil, is the most preferred member of this series and is of the 4S-configuration. It is particularly useful as an aldose reductase inhibitor in man for preventing or alleviating certain diabetes-associated chronic complications, including those of an ocular or neuritic nature (e.g., diabetic cataracts, retinopathy and neuropathy, etc.).

SUMMARY OF THE INVENTION

The present invention relates to certain novel 8-substituted derivatives of sorbinil, such as the 8-deutero, 8-tritio and 8-halo-substituted derivatives thereof. These compounds all have the 4S-configuration and are useful in the field of medicinal chemistry as aldose reductase inhibitors for the control of certain chronic diabetic complications. More specifically, the novel compounds of this invention are selected from the group consisting of the 4S-isomers of asymmetric spirohydantoins of the formula:

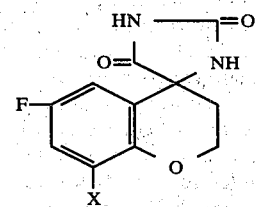

and the base salts thereof with pharmacologically acceptable cations, wherein X is deuterium, tritium or halogen (fluorine, chlorine, bromine or iodine). These novel compounds are aldose reductase inhibitors and therefore posses the ability to inhibit sorbitol accumulation in the lens and peripheral nerves of diabetic subjects. The labeled 8-deutero and 8-tritio derivatives are also especially useful in metabolism pharmacokinetic studies and in binding studies with the drug in animals and man. The 8-halo derivatives are useful as intermediates for preparing the labeled forms of the drug, in addition to being potent aldose reductase inhibitors per se.

Of especial interest in this connection are such typical and preferred member compounds of the invention as 4S-6-fluoro-8-deutero-spiro-[chroman-4,4'-imidazolidine]-2',5'-dione, 4S-6-fluoro-8-tritio-spiro-[chroman-4,4'-imidazolidine]-2',5'-dione, 4S-6,8-difluoro-spiro-[chroman-4,4'-imidazolidine]-2',5'-dione and 4S-6-fluoro-8-chloro-spiro-[chroman-4,4'-imidazolidine]-2',5'-dione.

DETAILED DESCRIPTION OF THE INVENTION

In accordance with the process employed for preparing the novel compounds of this invention, the known D-4S-6-fluoro-spiro-[chroman-4,4'-imidazolidine]-2',5'-dione (see U.S. Pat. No. 4,130,714) is (a) directly halogenated at the 8-position of the molecule and the resulting 6-fluoro-8-halo intermediate is thereafter (b) converted to the corresponding 6-fluoro-8-deutero or 6-fluoro-8-tritio final products by means of catalytic reduction procedures with either deuterium or tritium, as the case may be. In this way, 4S-6-fluoro-spiro-[chroman-4,4'-imidazolidine]-2',5'-dione is converted via 4S-6-fluoro-8-chloro-spiro-[chroman-4,4'-imidazolidine]-2',5'-dione to 4S-6-fluoro-8-deutero-spiro-[chroman-4,4'-imidazolidine]-2',5'-dione and 4S-6-fluoro-8-tritio-spiro-[chroman-4,4'-imidazolidine]-2',5'-dione, respectively.

The halogenation step in (a) is preferably effected by using conventional procedures, for example, by using elemental fluorine gas in nitrogen, or by using elemental chlorine or bromine optionally in the presence of a Friedel-Craft's catalyst such as ferric chloride, ferric bromide or iron powder, at a temperature that is generally in the range of about −50° C. to about 50° C., in a suitable reaction-inert organic solvent such as, for example, chloroform, nitrobenzene, dimethylformamide or glacial acetic acid, etc. Alternatively, chlorination or bromination may be carried out by simply using sulfuryl chloride or bromide, optionally in the presence of iodine as a catalyst, at a temperature that is generally in the same range as aforesaid and again in the presence of a suitable reaction-inert organic solvent, preferably glacial acetic acid or chloroform. Upon completion of the reaction, the desired 6-fluoro-8-halo intermediate is then recovered in a conventional manner and preferably by using known chromatographic techniques.

The 6-fluoro-8-halo intermediate product obtained in step (a) is then subjected to catalytic reduction as set forth in step (b) and this is preferably accomplished by using deuterium or tritium in conjunction with a noble metal catalyst such as palladium, usually suspended on a suitable catalyst support such as carbon or barium sulfate, etc. The preferred solvent for this reaction is generally a lower alkanol like methanol or ethanol or a cyclic ether such as dioxane or tetrahydrofuran. Upon completion of the reduction step, the catalyst is easily separated from the reaction mixture by filtration and the solvent thereafter removed from the resulting filtrate by means of evaporation under reduced pressure. In this way, a crude residual product is obtained that can easily be subjected to such standard purification techniques as column chromatography and the like to ultimately afford the desired final product (viz., the 8-labeled compound) in substantially pure form.

The chemical bases which are used as reagents to prepare the pharmaceutically acceptable base salts of this invention are those which form non-toxic base salts with the herein described acidic spiro-hydantoin compounds. These particular non-toxic base salts include those derived from such pharmacologically acceptable cations as sodium, potassium, calcium and magnesium, etc. These salts can easily be prepared by simply treating the aforementioned spiro-hydantoin acidic compounds with an aqueous solution of the desired pharmacologically acceptable cation, and then evaporating the resulting solution to dryness while preferably being placed under reduced pressure. Alternatively, they may be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

As previously indicated, the novel labeled 8-deutero and 8-tritio final products afforded by the process of this invention, like 4S-6-fluoro-8-tritio-spiro-[chroman-4,4'-imidazolidine]-2',5'-dione, are especially useful in metabolism pharmacokinetic studies and in binding studies with the drug in animals and man. The novel 8-halo derivatives, on the other hand, such as 4S-6-fluoro-8-chloro-spiro-[chroman-4,4'-imidazolidine]-2',5'-dione, are useful as intermediates for preparing the labeled forms of the drug, in addition to being potent aldose reductase inhibitors per se. Furthermore, the herein described compounds of this invention can be administered by either the oral or parenteral routes of administration. In general, these compounds are ordinarily administered in dosages ranging from about 0.05 mg. to about 10 mg. per kg. of body weight per day, although variations will necessarily occur depending upon the weight and condition of the subject being treated and the particular route of administration chosen. However, it is to be understood that the use of the 8-tritio derivative is necessarily restricted to use in animals or to trace amounts in man (for the aforesaid tracer studies) in view of its radioactivity.

In connection with the use of the asymmetric spiro-hydantoin compounds of this invention for the aforesaid purposes, it is to be noted that these compounds may be administered either alone or in combination with pharmaceutically acceptable carriers by either of the routes previously indicated, and that such administration can be carried out in either single or multiple dosages. More particularly, the compounds of this invention can be administered in a wide variety of different dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents. In general, the compounds of the invention will be present in such dosage forms at concentration levels ranging from about 0.5% to about 90% by weight of the total composition to provide the desired unit dosage.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes, and if so desired, emulsifying and/or suspending agents as well, together with such diluents as water, ethanol, propylene glycol, glycerin and various like combinations thereof.

For purposes of parenteral administration, solutions of these asymmetric spiro-hydantoins in sesame or peanut oil or in aqueous propylene glycol of N,N-dimethylformamide may be employed, as well as sterile aqueous solutions of the corresponding water-soluble, alkali metal or alkaline-earth metal salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all already obtainable by standard techniques well-known to those skilled in the art. Additionally, it is also possible to administer the aforesaid spiro-hydantoin compounds topically via an appropriate ophthalmic solution applied dropwise to the eye.

The activity of the compounds of the present invention, as agents for the control of chronic diabetic complications, is determined by their ability to successfully pass one or more of the following standard biological or pharmacological tests, viz., (1) measuring their ability to inhibit the enzyme activity of isolated aldose reductase; (2) measuring their ability to reduce or inhibit sorbitol accumulation in the sciatic nerve of acutely streptozotocinized (i.e., diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats, and (5) measuring their ability to delay cataract formation and reduce the severity of lens opacities in chronic galactosemic rats.

EXAMPLE 1

In a suitable reaction vessel, there were placed 2.00 g. (0.00847 mole) of 4S-6-fluoro-spiro-[chroman4,4'-imidazolidine]-2'5'-dione (prepared according to the procedure described in U.S. Pat. No. 4,130,714) dissolved in 100 ml. of glacial acetic acid at room temperature (~20° C.). The reaction vessel was fitted with a gas scrubbing apparatus comprised of an ethanol solution of aniline (10:1 by volume) and a 10% aqueous sodium hydroxide solution. A 10% fluorine in nitrogen (Matheson) solution of gas was then perfused through the mixture for a period of 60 minutes. After an additional 16 hours of perfusion with nitrogen, the resulting reaction mixture was concentrated in vacuo to an oil and thereafter triturated and subsequently vacuum evaporated with two-100 ml. portions of hexane. The foam thus obtained was next triturated with diethyl ether to yield a brown solid substance. The latter solid was subsequently recrystallized from freshly prepared 10% aqueous sodium bisulfite solution and the resulting product thereafter chromatographed on a 8μ Zorbax C-8 high pressure liquid chromatographic column, using an 85:15 by volume water acetonitrile solution as eluant. The appropriate fractions were then combined and subsequently concentrated in vacuo to afford to a residual liquid, which was later azeotroped with ethanol, then with ethyl acetate and finally with cyclohexane to ultimately afford a white powdery substance as the desired product. Recrystallization of the latter material from water then gave 13 mg. of pure 4S-6,8-difluoro-spiro-[chroman-4,4'-imidazolidine]-2',5'-dione, m.p. 198°-200° C. The pure product was further characterized by means of mass spectroscopy and nuclear magnetic resonance data, in addition to elemental analysis. Mass spectrum: m/e, 254(P).

EXAMPLE 2

To a solution consisting of 1.181 g. (0.00465 mole) of 4S-6-fluoro-spiro-[chroman-4,4'-imidazolidine]-2'5'-dione dissolved in 10 ml. of dimethylformamide (sieve dry) containing a trace of anhydrous ferric chloride, there was added at −40° C. a stream of chlorine gas over a period of 20 minutes. The resulting solution was then stirred at −20° C. for period of 2–2.5 hours and then allowed to warm slowly to room temperature (~20° C.) for another two hours. At this point, 50 ml. of water was slowly added to the reaction mixture, which was then stirred vigorously overnight at room temperature for a period of approximately 16 hours. Upon completion of this step, the spent mixture was next added to 100 ml. of ethyl acetate and the resulting aqueous phase therafter extracted with a fresh portion of ethyl acetate (25 ml.). The combined organic extracts were subsequently washed twice with brine and then dried over anhydrous magnesium sulfate. After removal of the drying agent by means of filtration and the solvent by means of evaporation under reduced pressure, there was finally obtained a golden yellow oil as the residual liquid. The latter oil was then chromatographed on a 230–400 mesh silica gel column (4.5×15.0 cm.) and eluted with ethyl acetate in 30 ml. fractions. Fraction No. 7 was concentrated to a colorless oil which eventually crystallized to a white solid (yield, 0.251 g.), m.p. 108°-114° C. Fraction No. 8 was concentrated to a colorless oil which, when triturated with petroleum ether, gave 0.196 g. (15.4%) of pure 4S-6-fluoro-8-chloro-spiro-[chroman-4,4'-imidazolidine]-2',5'-dione (as a white solid), m.p. 99°-102° C. (decomp.). Fraction No. 9 was concentrated to a clear oil which, when triturated with pentane, gave a white crystalline solid which also consisted of pure 4S-6-fluoro-8-chloro-spiro-[chroman-4,4-imidazolidine]-2',5'-dione, m.p. 100°-103° C. (decomp.); the yield of pure product from this fraction amounted to 0.257 g. (20.2%). The pure product from fraction No. 8 was further characterized by means of mass spectroscopy and nuclear magnetic resonance data, in addition to elemental analysis. Mass Spectrum: m/e, 272/270 (P+).

Anal. Calcd. for $C_{11}H_8Cl_2FN_2O_3 \cdot 1/3 H_2O$: C,47.75; H,3.16; N,10.13. Found: C,48.19; H,3.51; N,9.68

EXAMPLE 3

In a 35 ml. round-bottomed reaction flask, there was placed a solution consisting of 60 mg. (0.00022 mole) of 4S-6-fluoro-8-chloro-spiro-[chroman-4,4'-imidazolidine]-2',5'-dione (fraction No. 9 obtained in Example 2) dissolved in 4 ml. of ethanol. To this solution, there were then added 0.5 ml. of triethylamine and 100 mg. of 10% palladium on carbon catalyst. The resulting mixture was then treated with deuterium ($D_2$) gas in an atmospheric hydrogenator with stirring for a period of four hours. At the end of this time, stirring was discontinued and the reaction mixture was allowed to stand overnight at room temperature (~20° C.) for a period of approximately 16 hours. The contents were then removed from the hydrogenator, filtered through celite to remove the catalyst and finally concentrated in vacuo to afford a residual solid yellow product that was subsequently pumped under high vacuum for a period of one hour to give a white solid. The latter substance, which proved to be crude 4S-6-fluoro-8-deutero-spiro-[chroman-4,4'-imidazolidine]-2',5'-dione, was then chromatographed in the form of an ethyl acetate suspension on a 230–400 mesh silica gel column (5 ml. in a 10 ml. pipette) and thereafter eluted with 100% pure ethyl acetate, collecting 1.5 ml. fractions. Fractions 5–9 were found to contain pure product and were subsequently combined and concentrated in vacuo, followed by pumping under high vacuum to remove excess ethyl acetate and ultimately afford a white waxy solid. Recrystallization of the latter material from ethanol/diethyl ether than gave pure 4S-6-fluoro-8-deutero-spiro-[chroman-4,4'-imidazolidine]-2',5'-dione, m.p. 228°-231° C. The pure product was further characterized by means of mass spectroscopy, which on comparison with an authentic sample of pure 4S-6-fluoro-spiro-[chroman-4,4'-imidazolidine]-2',5'-dione, showed that 41% of the final product contains deuterium (i.e., 41% $^2H$ incorporation occurred in the deuteration step).

EXAMPLE 4

A solution consisting of 60 mg. (0.00022 mole) of 4S-6-fluoro-8-chloro-spiro-[chroman-4,4'-imidazolidine]-2',5'-dione (fraction No. 8 obtained in Example 2) dissolved in 4.0 ml. of ethanol containing 0.5 ml. of triethylamine was treated with 100 mg. of 10% palladium on carbon catalyst and stirred in a tritium atmosphere, using an atmospheric hydrogenator (atmospheric pressure) at room temperature (~20° C.) for a period of 18 hours. At the end of this time, the contents were stripped from the hydrogenator, excess tritium was removed by means of a methanol azeotrope and the catalyst was recovered from the reaction mixture by means of filtration. The resulting filtrate was then concentrated in vacuo and the residue redissolved in a mixture of 5 ml. of methanol and 5 ml. of benzene. At this point, thin layer chromatography (TLC) analysis, using 100% pure ethyl acetate as the eluant, showed no starting material to be present. The aforesaid solution, containing crude 4S-6-fluoro-8-tritio-spiro-[chroman-4,4'-imidazolidine]-2',5'-dione, was then concentrated in vacuo and subsequently redissolved in 0.5 ml. of pure ethyl acetate and chromatographed on a 230–400 mesh silica gel column (5 ml. in a 10 ml. pipette), using 100% pure ethyl acetate as the eluant. Fraction Nos. 6 and 7 containing single peak material (as determined by a radioscan of TLC plate) were then combined and subsequently concentrated in vacuo to ultimately afford pure 4S-6-fluoro-8-tritio-spiro-[chroman-4,4'-imidazolidine]-2',5'-dione. The pure product was found to contain 34.6% tritium on comparison with an authentic sample or pure starting material via radiochemical analysis (i.e., 34.6% $^3$H incorporation occurred during the course of the above reaction step).

EXAMPLE 5

The conversion of 4S-6,8-difluoro-spiro-[chroman-4,4'-imidazolidine]-2',5'-dione to 4S-6-fluoro-8-tritio-spiro-[chroman-4,4'-imidazolidine]-2',5'-dione is also accomplished by reduction over Raney nickel in aqueous potassium hydroxide using tritium gas according to the method of A. J. de Koning [Org. Prep. Proceed. Int., 7, 31–4 (1970)]. Purification of the desired final product is then achieved by using the same high pressure liquid chromatographic (HPLC) systems earlier employed in Example 1 to isolate the pure starting material. In this particular case, the corresponding final product obtained, viz., 4S-6-fluoro-8-tritio-spiro-[chroman-4,4'-imidazolidine]-2',5'-dione, is identical in every respect with the product of Example 4.

EXAMPLE 6

The following asymmetric spiro-hydantoin compounds of Examples 1 and 2, respectively, were tested at a concentration level of $10^{-6}$M for their ability to reduce or inhibit aldose reductase enzyme activity via the procedure of S. Hayman et al., as described in the *Journal of Biological Chemistry*, Vol. 240, p. 877(1965) and as modified by K. Sestanj et al. in U.S. Pat. No. 3,821,383. In each case, the substrate employed was partially purified aldose reductase enzyme obtained from calf lens. The results obtained with each compound are expressed below in terms of their percent inhibition of enzyme activity (%) with respect to the particular concentration level chosen ($10^{-6}$M):

| Compound | % Inhibition at $10^{-6}$M |
| --- | --- |
| Product of Example 1 | 74 |
| Product of Example 2 | 64 |

I claim:

1. A compound selected from the group consisting of the dextroratatory isomers of asymmetric spiro-hydantoins of the formula:

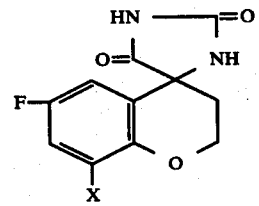

and the base salts thereof with pharmacologically acceptable cations, wherein X is deuterium or tritium.

2. A compound as claimed in claim 1 wherein X is deuterium.

3. A compound as claimed in claim 1 wherein X is tritium.

* * * * *